US 6,524,294 B1
United States Patent
Hilston et al.

(10) Patent No.: US 6,524,294 B1
(45) Date of Patent: Feb. 25, 2003

(54) Z-FOLD DIAPER FASTENER

(75) Inventors: Michael D. Hilston, Painesville, OH (US); Martin Smith, Los Angeles, CA (US); Karen L. Spilizewski, Euclid, OH (US); William G. Hartman, North Royalton, OH (US); Gary A. Avalon, Painesville, OH (US); David L. Savage, Painesville, OH (US); Roger H. Mann, Carona del Mar, CA (US); Linda Lin, Lyndhurst, OH (US)

(73) Assignee: Avery Dennison Corporation, Pasadena, CA (US)

(*) Notice: Subject to any disclaimer, the term of this patent is extended or adjusted under 35 U.S.C. 154(b) by 0 days.

(21) Appl. No.: 09/101,599

(22) PCT Filed: Jan. 16, 1997

(86) PCT No.: PCT/US97/00615

§ 371 (c)(1),
(2), (4) Date: Nov. 25, 1998

(87) PCT Pub. No.: WO97/25891

PCT Pub. Date: Jul. 24, 1997

Related U.S. Application Data

(60) Provisional application No. 60/010,029, filed on Jan. 16, 1996.

(51) Int. Cl.[7] .............................. A61F 13/15; A61F 13/20
(52) U.S. Cl. ...................... 604/386; 604/387; 604/389; 604/390; 604/391
(58) Field of Search .................. 604/385.01, 385.03, 604/386, 387, 390, 389, 391; 428/100, 343, 352

(56) References Cited

U.S. PATENT DOCUMENTS

| | | | |
|---|---|---|---|
| 3,748,701 A | 7/1973 | De Mestral | 24/204 |
| 3,800,796 A | 4/1974 | Jacob | 128/284 |
| 3,833,456 A | 9/1974 | Reed et al. | 161/167 |
| 3,932,328 A | 1/1976 | Korpman | 260/27 BB |
| 4,020,842 A | 5/1977 | Richman et al. | 128/287 |
| 4,051,853 A | 10/1977 | Egan, Jr. | 128/287 |
| 4,066,081 A | 1/1978 | Schaar | 128/287 |
| 4,169,303 A | 10/1979 | Lemelson | 24/204 |
| 4,465,717 A | 8/1984 | Crofts et al. | 428/40 |
| 4,662,875 A | 5/1987 | Hirotsu et al. | 604/389 |
| 4,710,190 A | 12/1987 | Wood et al. | 604/389 |
| 4,795,456 A * | 1/1989 | Borgers et al. | 604/390 |
| 4,869,724 A | 9/1989 | Scripps | 604/389 |
| 4,946,527 A * | 8/1990 | Battrell | 156/60 |
| 4,959,265 A | 9/1990 | Wood et al. | |
| 5,019,065 A | 5/1991 | Scripps | 604/385.1 |
| 5,051,259 A | 9/1991 | Olsen et al. | 424/443 |
| 5,053,028 A | 10/1991 | Zoia et al. | 604/385.1 |
| 5,057,097 A | 10/1991 | Gesp | 604/389 |
| 5,085,655 A | 2/1992 | Mann et al. | 604/389 |
| 5,106,384 A | 4/1992 | Polski | 604/390 |
| 5,133,707 A | 7/1992 | Rogers et al. | 604/389 |
| 5,141,790 A | 8/1992 | Calhoun et al. | |
| 5,531,731 A | 7/1996 | Brusky | 604/390 |
| 5,591,521 A | 1/1997 | Arakawa et al. | 428/352 |
| 5,636,414 A | 6/1997 | Litchholt | |
| 6,001,471 A * | 12/1999 | Bries et al. | 428/343 |

FOREIGN PATENT DOCUMENTS

EP  0 191 355  4/1989

* cited by examiner

*Primary Examiner*—Aaron J. Lewis
*Assistant Examiner*—Michele Kidwell
(74) *Attorney, Agent, or Firm*—Pearne & Gordon LLP

(57) ABSTRACT

Fastening systems for releasably securing two components together include tab and landing members. In a first arrangement, a Z-fold tab member has combined mechanical and adhesive engagement. A second arrangement includes adjacent adhesive and cohesive contact portions. A third arrangement contoured apertures and mechanical engaging elements. A fourth arrangement includes apertures and mechanical engaging elements sized and arranged so that each aperture receives a plurality of mechanical engaging elements. A fifth arrangement includes tab and landing members that cooperate to provide a color indicia of secure adhesive engagement.

5 Claims, 6 Drawing Sheets

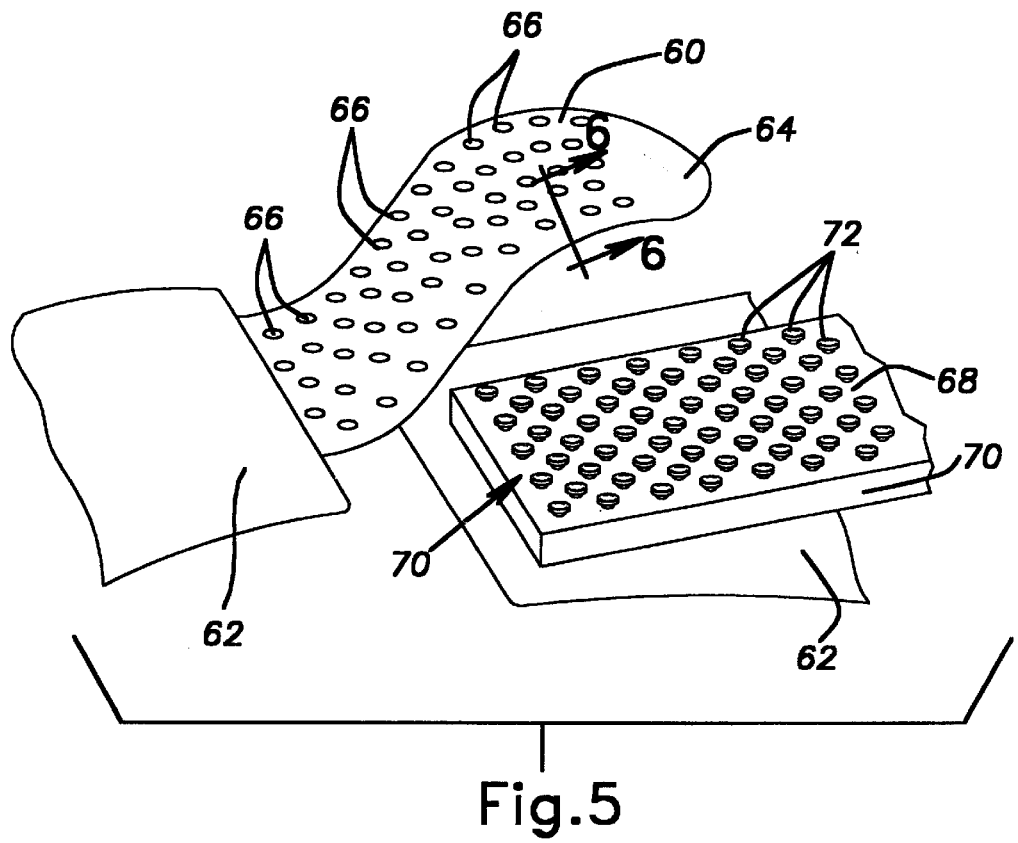
Fig.5
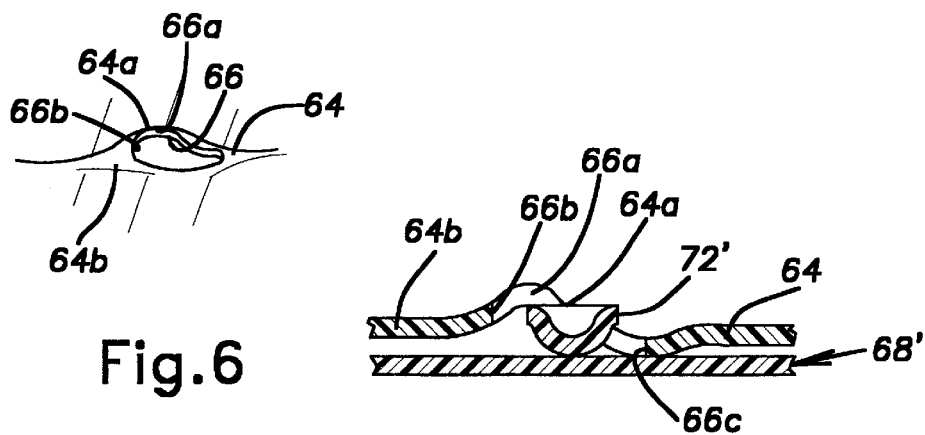
Fig.6
Fig.7

Z-FOLD DIAPER FASTENER

This application claims the priority of U.S. Provisional Application No. 60/010,029, filed Jan. 16, 1996.

BACKGROUND OF THE INVENTION AND RELATED ART

The present invention relates to closures for fastening adjacent portions of materials or components together. The closures are useful as fastening system closures for disposable diapers.

Diapers of this general type are widely used. A typical diaper construction comprises an absorbent pad or batt or the like enclosed in an outer plastic shell or a non-woven backsheet that is non-woven fabric laminated with a water impermeable layer such as a polyethylene film. A water permeable inner shell or liner is also provided to promote separation of fluid from the user.

The fastener tape system generally includes adhesive tabs fastened to one end of the diaper assembly construction at each lateral side of the diaper in a permanent "factory joint" by the diaper manufacturer using adhesives or other techniques. The tabs have a face coated with pressure-sensitive adhesive. The tabs are releasably attachable to the other end of the diaper at each lateral side in a "user joint". The attachment is releasable both to allow permanent removal of the diaper and to allow unfastening to inspect the diaper followed by refastening if indicated.

The user joint may be formed by direct connection of the tab to the diaper outer surface whether the latter is formed of a plastic film or a non-woven backsheet. In the case of plastic film shells, it is typical to provide a "landing zone or member" formed of reinforcing tape or the like for receiving the end of the tab to form the user joint. The landing zone may provide a plastic surface or a non-woven surface and may comprise a knit type fabric landing pad.

The fastener tape system may rely solely upon pressure-sensitive adhesive in the formation of the user joint as shown in U.S. Pat. Nos. 4,795,456, 4,710,190, 4,020,842 and 3,833,456. The use of combined adhesive and mechanical fastener systems is shown in U.S. Pat. Nos. 5,019,065, 5,053,028 and 4,869,724. The teachings of all of these patents being incorporated herein by reference.

The use of extensible or stretchable tabs to promote user comfort through better fit and more secure mounting is also known in the art. The tabs operate as extensible diaper side waistbands. Examples of such diaper fastening systems are disclosed in U.S. Pat. Nos. 4,795,456, 4,066,081, 4,051,853 and 3,800,796. The teachings of these patents being incorporated herein by reference.

Related art includes U.S. Pat. Nos. 4,465,717, 4,662,875, 5,051,259, 5,106,384, 5,133,707, 5,531,731, 5,591,521 and European Publication No. 0 191 355.

SUMMARY OF THE INVENTION

The present invention has a number of different aspects relating to improvements in diaper tab fastening systems. These improvements may be used alone or in combination in a fastener system. The fastener system may include an extensible or substantially nonextensible element or tab member.

In a first aspect, the fastening system includes overlying or spatially combined adhesive and mechanical fastening attachments in a tab having an efficient Z-fold configuration. Upon deployment of such tab arrangement to close the diaper, the adhesive provides immediate tack strength and the mechanical attachment provides improved shear strength. The mechanical and adhesive attachments each contribute to the total integrity or strength of the diaper closure or user joint, and neither has to be fully effective to provide the required total closure strength.

In a second aspect, the fastening system has a combined adhesive closure system including both adhesive and cohesive elastomers to effect closure. In this manner, the aggressiveness of adhesives is attained as well as the contaminate resistance of cohesives.

In a third aspect, the fastening system includes a mechanical fastening system having mechanically engaging elements adapted to be received in contoured or obliquely extending apertures in the tab. The mechanical engaging elements have shaped base portions extending to head portions for interengagment within the apertures.

In a fourth aspect, the fastening system includes a mechanical fastening system having an open mesh tab adapted to receive a plurality of mechanical engaging elements. The apertures and mechanical engaging elements are sized and arranged to provide engagement of a plurality of elements in each of the apertures.

In a fifth aspect, the fastening system includes a color indication of proper adhesive engagement of the tab and landing members.

BRIEF DESCRIPTION OF THE DRAWINGS

FIG. 5 is a fragmentary perspective view showing a diaper having a fastener system including a tab member in the deployed condition ready for securement to a landing member in accordance with a further embodiment of the present invention;

FIG. 6 is a fragmentary sectional view on an enlarged scale taken along the line 6—6 in FIG. 5;

FIG. 7 is a fragmentary sectional view similar to FIG. 6 showing the tab and landing members of FIG. 5 in a securement position;

DETAILED DESCRIPTION OF THE INVENTION

Figure 1:
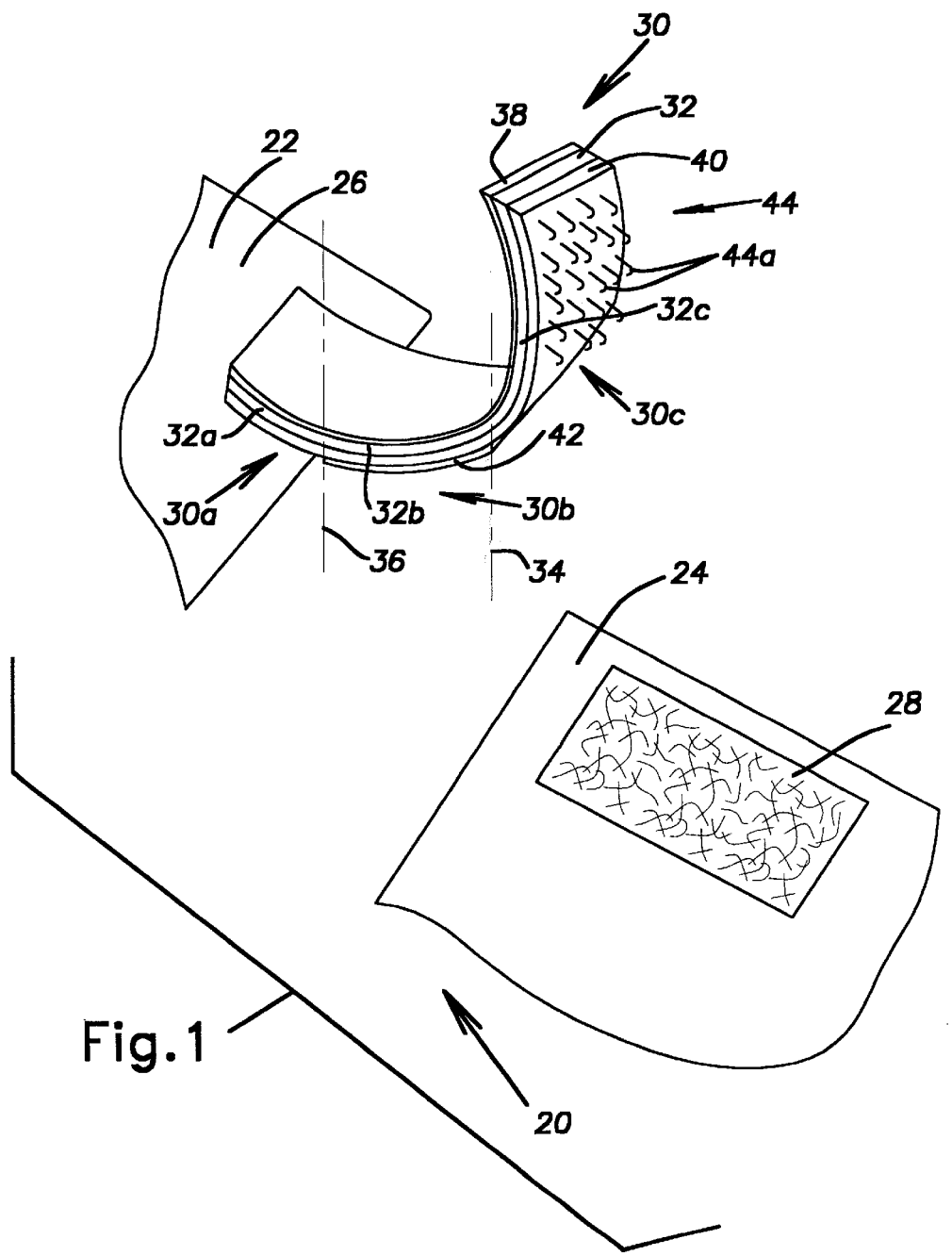
FIG. 1 is a fragmentary perspective view showing a diaper having a fastener system including a tab member in the deployed condition ready for securement to a landing member in accordance with the present invention.

Herein, pressure-sensitive adhesive layers or applications are variously referred to in the tab fastener systems. The adhesive layer or application may be provided using known adhesive materials such as pressure-sensitive adhesives including acrylic resin and natural or synthetic based rubber adhesives. Preferred adhesives include hot melt pressure-sensitive adhesives of the A-B-A block copolymer type comprising an elastomeric B-block derived from isoprene and thermoplastic A-blocks derived from styrene as disclosed in U.S. Pat. No. 3,932,328. Illustrative rubber based adhesives include styrene-isoprene-styrene and styrene-butadiene-styrene which may optionally contain diblock components such as styrene isoprene and styrene butadiene. The adhesives may be applied using hot-melt, solvent or emulsion techniques.

The provision of extensible facestock layers and/or tab constructions referred to herein may be formed or provided in any of the following manners.

The facestock film may be made extensible or stretchable by forming it of extrudable elastomers such as the thermoplastic elastomers sold by the Shell Chemical Company under the designation Kraton. These elastomers may be SBS, SIS, SI, $S(IS)_X$ and SEBS block copolymers and mixtures thereof. The facestock may also be formed of a polyurethane, polyethylene and polypropylene copolymer or EVA polymer of suitable elastic characteristics. The resulting facestock or tab should have an extensibility or elasticity similar to that of the films disclosed in U.S. Pat. No. 5,057,097 to Gesp, and owned by the assignee herein.

The extensibility may also be provided by coextrusion processing with combinations of extensible and nonextensible polymers. More particularly, a side-by-side coextrusion including adjacent portions of extensible polymer film and nonextensible polymer film may be made. The diaper tab may be cut from the coextruded film and include one or more extensible film portions extending across the width of the tab. The coextrusion processing requires a matching or near matching of the melt flow characteristics of the polymers forming the facestock. Such matching and processing techniques are known in the art and illustrated, for example, in U.S. Pat. No. 3,800,796.

The facestock may comprise an extensible fabric such as a stretchable non-woven or woven fabric. Preferably, the fabric has a higher tensile modulus and is less extensible in the fabric manufacture machine direction than in the cross direction. This will facilitate handling of the fabric web in adhesive coating and cutting processing. The tabs may be cut across the width or in the cross machine direction of fabric manufacture. Suitable non-woven fabrics are commercially available. For example, Kimberly-Clark Corporation of Neenah, Wisconsin markets a suitable fabric under the name Demique. A suitable polyurethane non-woven fabric is sold by Kanebo Company of Japan. Suitable woven fabrics are commercially by Bloomburg Mills of Bloomburg, Pa. and the Comco Company of Charlotte, N.C.

The tab may be nonextensible and formed of conventional polymers such as polypropylene, polyethylene and blends of copolymers thereof. Such tabs typically include an extruded facestock layer or film formed of such polymers.

Figure 2:
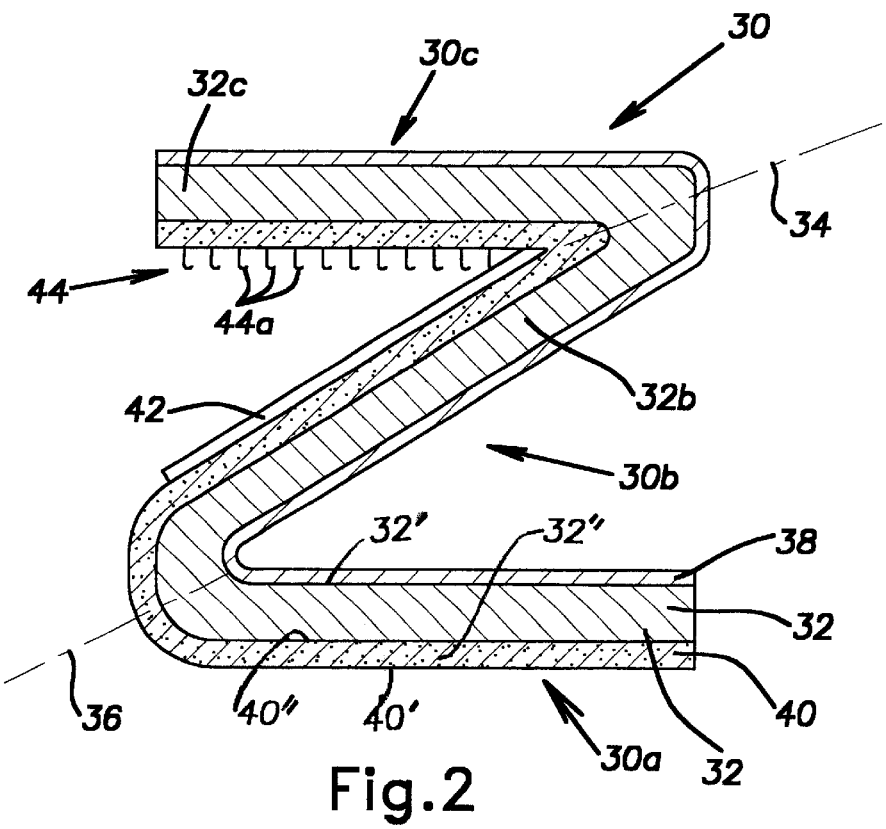
FIG. 2 is an elevational view of the tab member of FIG. 1 in the storage position with the folded portions slightly spaced for clarity of illustration.

Referring to FIGS. 1 and 2, a fastener system 20 for releasably closing a diaper 22 having opposed longitudinal diaper ends 24 and 26 is shown. The fastener system includes a landing member 28 mounted to the longitudinal diaper end 24 and a diaper tab 30 mounted to the longitudinal diaper end 26. The tab 30 includes an extensible facestock layer 32 having intermediate fold lines or planes 34 and 36. The fold lines 34 and 36 divide the tab 30 and facestock layer 32 into a terminal or mounting portion 30a and 32a, a connecting or central portion 30b and 32b, and a terminal or securement portion 30c and 32c. The facestock layer 32 is extensible and may be formed in any of the above described manners.

Release means or coating 38, such as a silicone coating, as are known in the art, extends along an outer surface 32' of the facestock layer 32. The other or inner surface 32" of the facestock layer has an adhesive layer 40 extending along its entire length adjacent the portions 30a, 30b and 30c of the tab 30. The adhesive layer 40 has an outer surface 40' and an opposed inner surface 40". The adhesive layer 40 may comprise a known pressure-sensitive adhesive suitable for use in diaper tab applications as described above.

Figure 3:
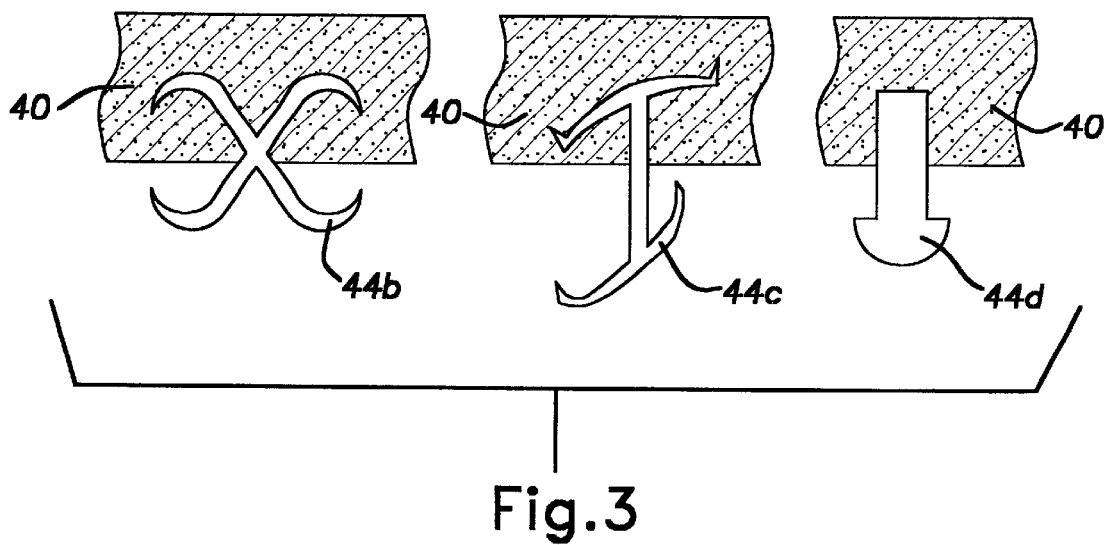
FIG. 3 is a schematic perspective view of various mechanical fastener elements that may be used in the fastener system of FIG. 1.

One portion of the adhesive layer 40 extending along the terminal or mounting portion 30a, on the left as shown in FIG. 3, is exposed to form a factory joint with the diaper outer shell of the diaper 22. A release means or coating 42, which may be similar to the release means 38, extends along the adhesive layer 40, or more particularly, the outer surface 40' thereof, across the central or connecting portion 30b of the tab 30. Mechanical engagement member 44 is located adjacent the terminal segment 30c, the portion of the adhesive layer 40 and mechanical engagement member 44 being coextensive along such terminal or securement portion of the tab 30.

As shown, the mechanical engagement member 44 comprises a plurality of engagement elements 44a that project from the facestock layer 32. The elements 44a may be integrally formed with the facestock layer 32, or they may be separately formed and subsequently attached thereto as a conventional hook and loop fabric. It is also possible to embed separate elements 44b, 44c or 44d in the adhesive layer 40 as shown in FIG. 3. (A variety of such elements are shown in U.S. Pat. Nos. 3,748,701 and 4,169,303.) The elements 44a–44d extend a sufficient distance beyond the outer surface 40' of the adhesive layer 40 to provide mechanical engagement with a locking or complimentary array of mechanical elements, or with a fibrous material such as a non-woven landing tape or zone, or with a non-woven backsheet of a diaper.

The tab 30 provides a known "Z-fold" configuration as particularly shown in FIG. 2. However, the added advantages of extensibility and combined mechanical/adhesive engagement are provided in accordance with the invention.

Figure 4:
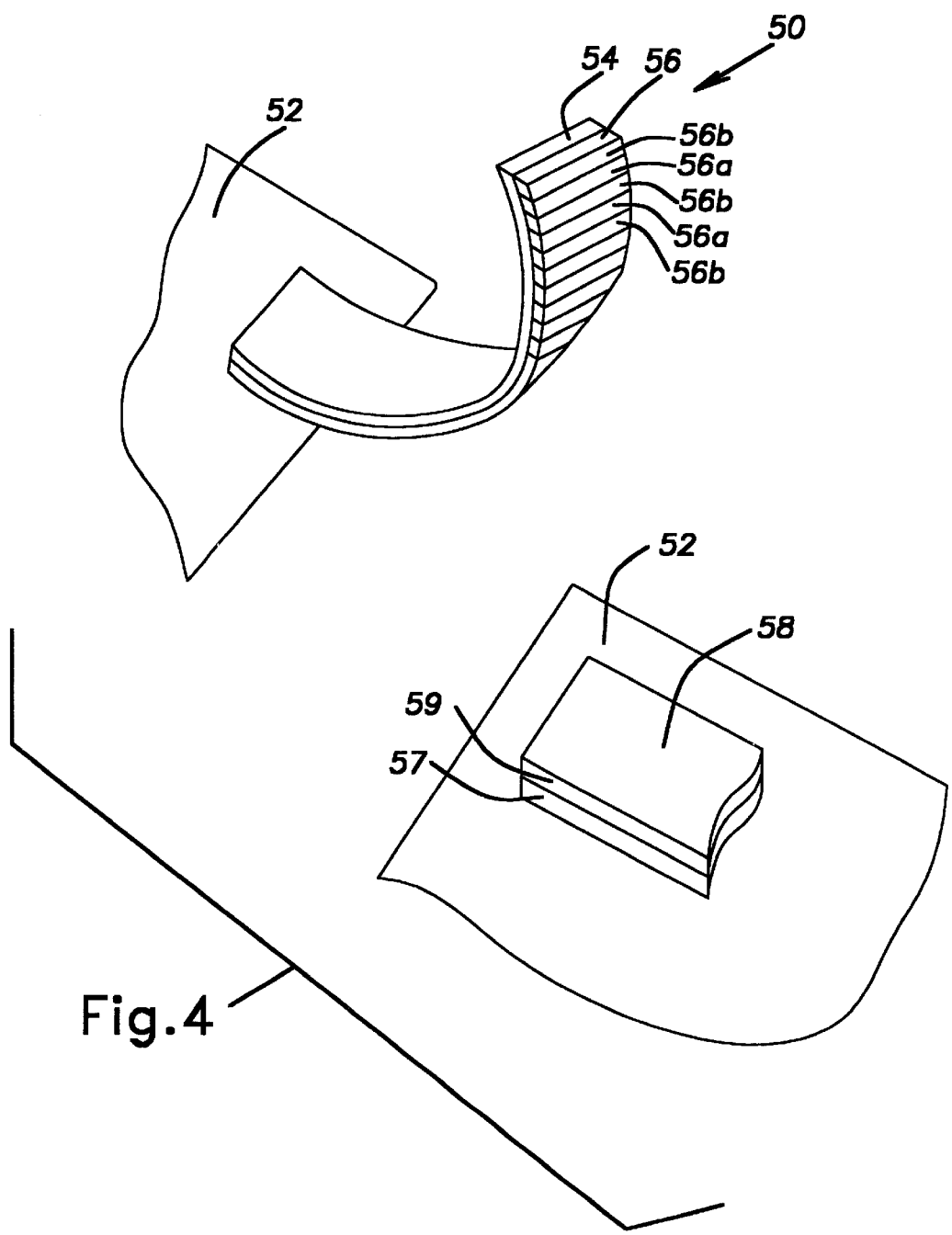
FIG. 4 is a fragmentary perspective view showing a diaper having a fastener system including a tab member in the deployed condition ready for securement to a landing member in accordance with another embodiment of the present invention.

Referring to FIG. 4, a second aspect of the present invention is illustrated. Accordingly, a diaper tab 50 for use in closure of a diaper 52 is shown. The diaper tab 50 includes a facestock film or member 54 and an adhesive/cohesive layer 56. The tab 50 is arranged to engage a landing zone tape or member 58 secured to the opposite end of the diaper for closure thereof. The tape 58 includes a cohesive layer 59 carried by a supporting facestock layer 57 adhered to the outer shell of the diaper 52.

The adhesive/cohesive layer 56 includes adhesive portions 56a and cohesive portions 56b. These portions are shown in an alternating row or strip pattern, however, any pattern may be used. The relative surface areas of the portions 56a and 56b are not critical, but each should be sufficient to achieve the desired characteristic thereof. For example, a 1:1 surface area ratio is generally satisfactory, but this may vary depending upon the aggressiveness of the pressure-sensitive adhesive, tack of the cohesive and/or the contamination resistance of the cohesive.

The adhesive portions 56a may be formed of an above described pressure-sensitive adhesive. The cohesive portions may be formed of the cohesive elastomers described in U.S. Pat. No. 5,085,655 to Mann, owned by the assignee herein. Similarly, the cohesive layer 59 of the landing zone tape 58 may also be provided in accordance with the Mann patent.

The adhesive/cohesive layer 56 provides the aggressiveness of pressure-sensitive adhesives and the contaminate resistance of cohesives. Also, it should be appreciated that the adhesive portions of the layer 56 allow the tab 50 to be secured to any available surface of a soiled diaper that has been rolled-up for disposal. The adhesive/cohesive layer 56 may be formed using the side-by-side coextrusion process discussed above with respect to the provision of extensible facestock or tab constructions.

Referring to FIGS. 5, 6 and 7, the fourth aspect of the present invention is illustrated in connection with a diaper tab 60 for use in the releasable closure of a diaper 62. The diaper tab 60 includes a facestock film or member 64 having a plurality of perforations or apertures 66 in aligned rows and columns in a regular array. The tab 60 is arranged to engage a landing zone tape or member 68 secured to the opposite end of the diaper 62 for closure thereof. The tape 68 includes a substrate film 70 having a plurality of upstanding engaging elements 72 arranged in a complementary pattern or array and adapted to be received in the apertures 66 to secure the diaper closed. The substrate film 70 may be secured to the diaper 62 by adhesive or other means known in the art.

As best shown in FIG. 6, the facestock film 64 may be provided with a non-planar configuration to better present the apertures 66 for receipt of the elements 72. For example, the aperture 66 extends in an angulated portion 64a of the facestock film 64 which extends at an angle relative to base portion 64b of the film 64. The angulated portion 64a extends in a plane that intersects the plane of the base portion 64b. Since the major portion of the aperture 66 is within the angulated plane, the aperture is said to be generally contained in the angulated plane even though portions of the aperture extend out of the plane.

The film 64 may be heat set by hot rolling to provide the desired non-planar configuration and to effectively sculpture the aperture in the direction of element engagement and locking. The film 64 may be formed of suitable polymer material to provide a substantially nonextensible or an extensible tab as particularly discussed below.

The apertures 66 may of circular cross section (prior to heat setting) as shown. The aperture 66 has an opening edge 66a including an upper edge portion 66b and a lower edge portion 66c. The elements 72 project to a height intermediate the upper and lower edge portions. Accordingly for securement or diaper closure, the tab member 60 is initially moved with tension in a lengthwise direction (to the right in FIG. 7) over and past the securement point, the tab member is then moved downwardly to position the base portion 64b of the facestock film 64 on the substrate 70 of the landing member 68. Upon relaxation of the tension, the tab member withdraws slightly to the left as shown in FIG. 7, and the elements 72 are initially received in the apertures 66 adjacent the upper edge portion 66b to facilitate engagement. The lower edge portion 66c enhances retention of the elements 72. Further, the apertures 66 may be of key hole shape including a narrowed end portion extending to a relatively wider portion. The elements 72 are initially received in the wider portion of the key hole shaped aperture and then better trapped in the narrow portion of the key hole to improve the security of the closure. This improved entrapment is particularly effective when the film 64 is extensible and tensioned in the closed position.

The elements 72 may have any shape that is conveniently snagged or received in the apertures 66 as the tab 60 is pressed against and moved across the landing zone tape 68. Preferably, the elements 72 comprise discrete non-fibrous members. The elements 72 are shown with a mushroom shape in FIG. 5, the enlarged head operating to maintain engagement within the aperture. In FIG. 7, landing zone tape 68' provides elements 72' having a bowl shape. As illustrated, the elements 72, 72' and apertures 66 are sized and arranged to engage in pairs.

The number, size and distribution of the apertures 66 and elements 72 are not critical. The number of engaged apertures and elements upon securement may range from one to 500. The major dimensions of the apertures 66 and elements 72 may each range from about 0.005" to 0.5".

The landing zone tapes 68, 68' and/or the elements 72, 72' may be formed of any polymer of suitable stiffness or rigidity to assure good mechanical shear strength. For example, polyurethane, nylon, polyethylene and polypropylene are sufficiently rigid. Also, these polymers may be extruded onto a rotating mold to simultaneously form the substrate film and the engaging elements.

Figure 8:
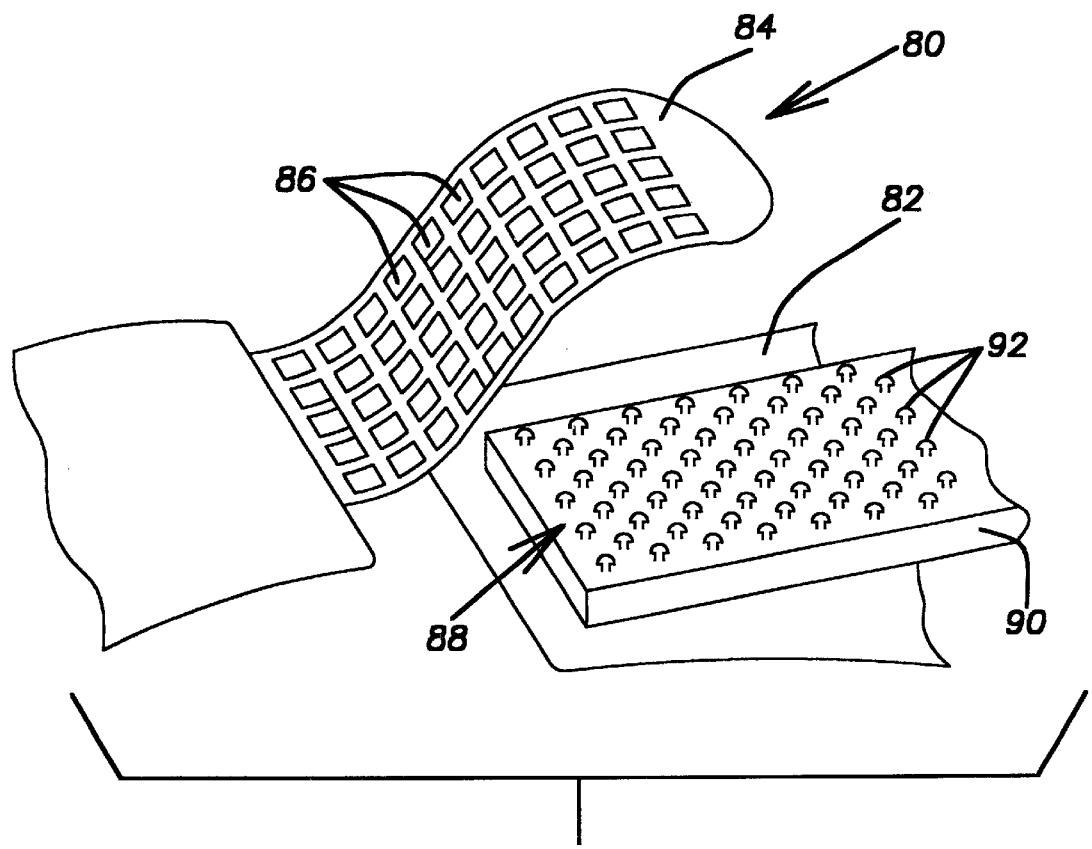
FIG. 8 is a fragmentary perspective view showing a diaper having a fastener system including a tab member in the deployed condition ready for securement to a landing member in accordance with yet a further embodiment of the present invention.
Figure 9:
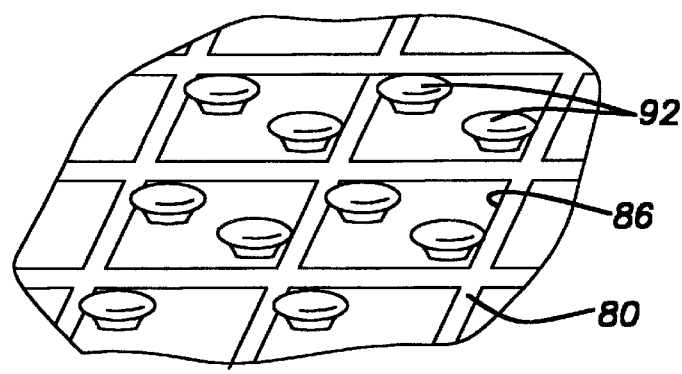
FIG. 9 is a fragmentary elevational view on an enlarged scale showing the tab and landing members of FIG. 8 in a securement position.

Referring to FIGS. 8 and 9, a fourth aspect of the invention is illustrated in connection with a diaper tab 80 for use in closure of a diaper 82. The diaper tab 80 includes a facestock film or member 84 having a plurality of perforations or apertures 86 arranged in a regular array of aligned rows and columns. The tab 80 is arranged to engage a landing zone tape 88 secured to the opposite end of the diaper 82 for closure thereof. The tape 88 includes a substrate film 90 having a plurality of upstanding engaging elements 92 adapted to be received in the apertures 86 to secure the diaper closed. Preferably, the elements 92 comprise discrete non-fibrous members. The substrate film 90 may be secured to the diaper 82 by adhesive or other means known in the art.

The apertures 86 in the facestock film 84 substantially provide the latter with an open, mesh type construction. As compared with the tab 60, the tab 80 is substantially more open, the apertures 86 being relatively larger than the apertures 66. Although the apertures 86 are shown with a rectangular shape, they may have any configuration.

The elements 92 have a mushroom configuration, the mushroom head enhancing interlocking within the apertures 86. The elements 92 may have any shape that is conveniently received in the apertures 86 as the tab 80 is pressed against and moved across the landing zone tape 88.

The apertures 86 and elements 92 are relatively sized and arranged to engage more than one element in an aperture. In FIG. 9, two elements 92 are received in each aperture 86. However, three or more elements may be received in a single aperture. The actual size of the apertures and elements may be similar to those last described above.

The tab 80 and landing zone tape 88 may be formed of materials similar to those described above in respect to the tab 60 and tape 68. Also, similar processing techniques may be used to make the tab and tape.

Figure 10:
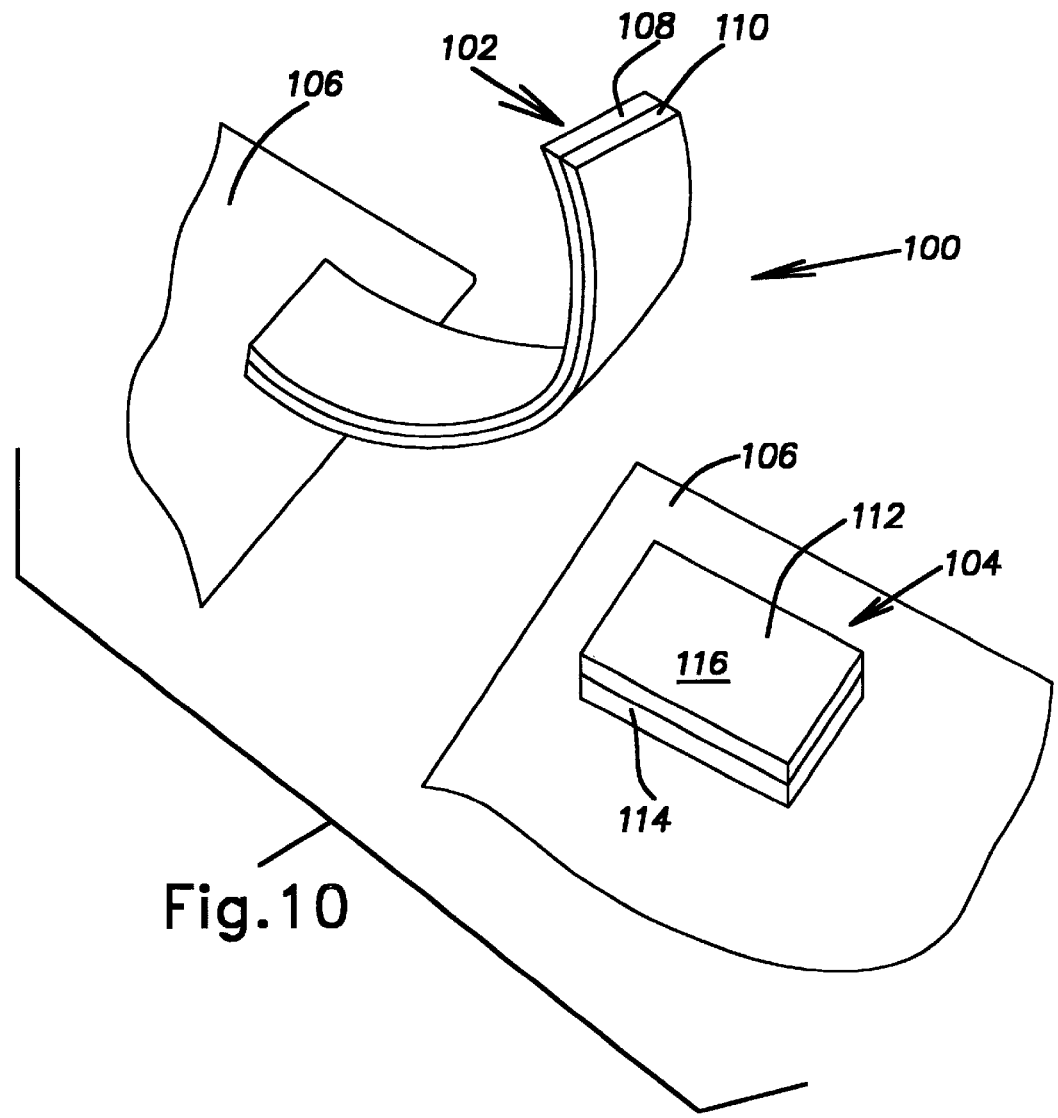
FIG. 10 is a fragmentary perspective view showing a diaper having a fastener system including a tab member in the deployed condition ready for securement to a landing member in accordance with yet a further embodiment of the present invention.
Figure 11:
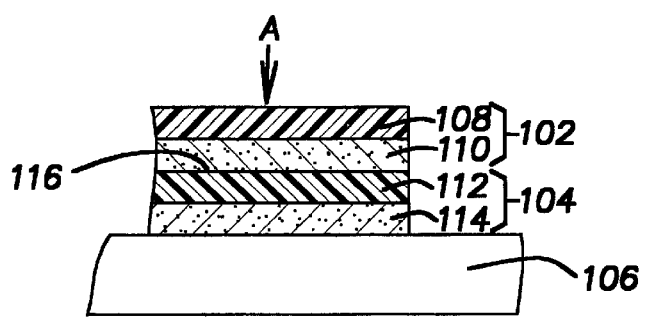
FIG. 11 is a fragmentary sectional view on an enlarged scale showing the tab and landing member of FIG. 10 adhesively engaged.

Referring to FIGS. 10 and 11, a fastener system 100 includes a diaper tab member 102 deployed for engagement with a landing member 104 to releasably close the diaper 106. The diaper tab 102 includes a facestock film or member 108 having a pressure-sensitive adhesive layer 110. The tab 102 may be nonextensible or extensible. The landing member 104 includes a facestock film or member 112 secured to the outer shell of the diaper 106 in a suitable manner such as by pressure-sensitive adhesive layer 114.

The facestock film 108 is clear or transparent and the adhesive layer 110 is tinted to provide it with a suitable color, e.g. a yellow color, which may be viewed through the facestock film 108. The transparency of the film 108 may be achieved by omission of typical opacifying agents. The coloration of the adhesive layer 110 may be provided by the addition of suitable dyes or pigments to the adhesive composition.

The facestock layer 112 of the landing member 104 provides an exposed or outer adherent surface 116 having a color that cooperates with the color of the layer 110 when viewed through the transparent facestock layer 108 to provide a color indication of proper adhesive engagement and diaper closure. To that end, the facestock layer 112 and/or the adherent surface 116 thereof may be colored by conventional dyes or pigments incorporated in the facestock composition during manufacture or later applied to the adherent surface 116. For example, the adherent surface 116 may be colored blue.

The color intensities are selected so that upon placement of the tab 102 and landing member 104 in close overlying relationship characterizing proper or desired adhesive engagement and diaper securement, the tab 102 appears to be green when viewed through the clear facestock film 108. For example, referring to FIG. 11, the diaper tab 102 and the landing member 104 are shown in cross-section. When secure engagement is provided, the tab 102 assumes a green color when viewed in the direction of the arrow A.

As an alternative to color change, the tab 10 may have a hazy or cloudy appearance which becomes clear or transparent upon secure engagement with the landing member 104.

It should be evident that this disclosure is by way of example and that various changes may be made by adding, modifying or eliminating details without departing from the fair scope of the teaching contained in this disclosure. The invention is therefore not limited to particular details of this disclosure except to the extent that the following claims are necessarily so limited.

What is claimed is:

1. A diaper fastening system for releasably securing first and second longitudinal ends of a diaper together, said fastening system including tab and landing members respectively mounted to said first and second longitudinal ends of said diaper, said tab member having a mounting portion, a connecting portion and a securement portion, said tab member being foldable to a Z-shape in a storage position and being deployable to a securement position to provide combined mechanical and adhesive securement with said landing member, said tab member including a facestock member having opposed inner and outer facestock surfaces, an adhesive layer having opposed inner and outer adhesive surfaces, said adhesive layer extending continuously along said facestock member adjacent said mounting, connecting and securement portions of said tab member and having said inner adhesive surface adjacent said inner facestock surface, a first release coating extending continuously along said outer adhesive surface adjacent said connecting portion, a second release coating extending continuously along the entire width and length of said outer facestock surface adjacent said mounting, connecting and securement portions of said tab member, mechanical fastening elements projecting from said outer adhesive surface adjacent said securement portion, said mounting portion being folded toward said connecting portion with said outer adhesive surface adjacent said mounting portion being secured to said first longitudinal diaper end and said securement portion being folded toward said first release coating and said connecting portion when said tab member is folded in said storage position, said securement portion being unfolded away from said first release coating to expose said outer adhesive surface and mechanical fastening elements adjacent said securement portion upon deployment of said tab member to said securement position, and said landing member including contact surface means for adhesive engagement by said outer adhesive surface adjacent said securement portion to provide immediate tack strength and mechanical engaging means for mechanical locking engagement by said mechanical fastening elements to provide shear strength, whereby said tab member and said landing member in said securement position provide combined adhesive and mechanical securement between said tab member and said landing member.

2. A diaper fastening system as in claim 1, wherein said mechanical fastening elements comprise hooks.

3. A diaper fastening system as in claim 1, wherein said mechanical fastening elements comprise separate hook elements embedded in said adhesive layer adjacent said securement portion.

4. A diaper fastening system as in claim 1, said tab member is extensible.

5. A diaper fastening system as in claim 1, wherein said mechanical fastening elements comprise hooks, said landing member comprises loops or fibrous material providing said mechanical engaging means and contact surface means.

* * * * *